United States Patent [19]

Hawari et al.

[11] Patent Number: 4,950,833

[45] Date of Patent: Aug. 21, 1990

[54] PROCESS FOR THE REDUCTIVE DEHALOGENATION OF POLYHALOAROMATICS

[75] Inventors: Jalal A. Hawari, Ville St-Laurent; Réjean Samson, Fabreville Laval, both of Canada

[73] Assignee: Her Majesty the Queen in right of Canada, as represented by the National Research Council of Canada, Ottawa, Canada

[21] Appl. No.: 413,942

[22] Filed: Sep. 28, 1989

[51] Int. Cl.$^5$ .............................................. C07C 1/20
[52] U.S. Cl. .............................. 585/469; 208/262.5; 210/909
[58] Field of Search .................... 585/469; 208/262.5; 210/909

[56] References Cited

U.S. PATENT DOCUMENTS

| | | | |
|---|---|---|---|
| 4,340,471 | 7/1982 | Jordan | 208/262.5 |
| 4,377,471 | 3/1983 | Brown et al. | 208/262.5 |
| 4,379,746 | 4/1983 | Norman et al. | 208/262.5 |
| 4,416,767 | 11/1983 | Jordan | 208/262.5 |

Primary Examiner—Asok Pal
Assistant Examiner—J. Saba
Attorney, Agent, or Firm—Ratner & Prestia

[57] ABSTRACT

The present invention relates to a process for the reductive dehalogenation of polyhaloaromatic compounds. It comprises reacting polyhaloaromatics in a hydrocarbon or silicone-based oil or an organic diluent, with an alkali metal in the presence of an ammonium salt to reduce the polyhaloaromatics to hydrogenated aromatics and to convert the halogen content to metal halides. Preferably, the polyhaloaromatics and the ammonium salt are to be reacted with the alkali metal in the form of a suspension. Other preferred features include the use of an amount of alkali metal ranging from 5 to 10 moles and the use of an amount of ammonium salt also ranging from 5 to 10 moles for each mole of the polyhaloaromatic compound to be reduced, carrying out the reaction under an inert atmosphere and carrying out the reaction at a temperature ranging from 40° to 60° C.

10 Claims, No Drawings

PROCESS FOR THE REDUCTIVE DEHALOGENATION OF POLYHALOAROMATICS

FIELD OF THE INVENTION

The present invention relates to a process useful to reduce polyhaloaromatics such as PCBs. The compounds are reduced using an alkali metal and an ammonium salt at low temperature.

BACKGROUND OF THE INVENTION

Polyhaloaromatics such as polychlorinated biphenyls are organic chemicals that have been widely produced at the beginning of the 20th century. These compounds possess excellent heat stability, are nonflammable in nature, have low volatility and good viscosity characteristics at operating temperatures. These properties made certain polyhaloaromatics ideal for use as dielectric materials for transformers and capacitors. These compounds have also been used as efficient heat transfer agents.

However, extensive studies on halogenated biphenyls have shown that the excellent stability of these products made their presence in the environment hazardous and the compounds have been positively identified as possible carcinogens. Accordingly, a number of countries such as the United States now prohibit manufacture, importation or use of these compounds on their territory. Furthermore, extensive programs to remove and destroy most of the compounds produced so far have been established.

PCBs have been mainly used in electrical insulating oils contained in electrical transformers, capacitors, underground cables and the like. This was the most important use for these materials that have in many instances been replaced with different non-hazardous materials. Hence, the need to find a safe and efficient method to reduce PCBs to environmentally safe compounds became quite obvious. In that respect, the scientific literature provides an extremely broad array of processes aimed at dehalogenating organic halides.

So far, it seems that the most economically feasible process for dehalogenating PCBs is their conversion into non-toxic compounds through incineration at high temperatures, usually above 1000° C. Obviously, this combustion must be carried out in specially designed high temperature furnaces. Also, the combustion process yields the formation of gases that must be vented into the atmosphere. However, if the combustion is incomplete or interrupted, extremely toxic compounds such as polychlorinated dibenzofurans may be produced.

A large number of prior art documents describe processes for dehalogenating organic halides at moderate temperatures ranging between 80° and 200° C. which involve contacting an organic halide solution with small particles of alkali metals. Such processes are described in the following references: E.P No. 0099951, Journal of Hazardous Materials, 12, 1985, 161-176 (A. Cornel et al), U.S. Pat. No. 4,379,746, U.S Pat. No. 4,340,471, U.S. Pat. No. 4,377,471, U.S. Pat. No. 4,416,767, Japanese Patent No. 49082570, Can. Patent No. 1,185,265 and Can. Patent No. 1,179,381.

In these references, whether the alkali metal is used alone or in conjunction with another compound, complete dehalogenation is rarely obtained and the processes often lead to polymerization. It is also worth mentioning that although in some instances processes using an alkali metal either alone or with other substances are successful in dehalogenating organic halides, the usual temperature at which the process must be performed generally remains quite above room temperature.

Furthermore, most methods that were developed to degrade PCBs in alkali metal media involve the use of coreagents that are expensive, sensitive to impurities and hazardous to the environment. For example, degradation of PCBs in silicon-based oil, benzophenone, alkylbiphenyls, naphthalene or anthracene, requires careful separation of these chemicals at the end of the reaction before any safe disposal into the environment can be foreseen.

In a recently published article, K.M. Anwer et al (J. Org. Chem., 54, 1284–1289, 1989) describe a reaction through which chloroaromatics are dechlorinated using ammonium formate on a supported Pd/C catalyst. This reaction requires the use of expensive catalysts that are sensitive to impurities. It is also worth mentioning that dechlorination is influenced by the solvent. For example, dechlorination of 1-Cl-naphthalene was only 51% complete in tetrahydrofurans (THF).

Finally, organic reductions by alkali metals in neat ammonia require special equipment and careful precautions to handle ammonia gas. Furthermore, when organic halides, particularly aromatic halides, are reduced by sodium and neat ammonia, they often produce toxic aromatic amines in a complex pool of other products.

Therefore, it would be highly desirable to provide a process efficient to successfully dehalogenate organic halides using inexpensive reagents while producing environmentally safe by-products.

SUMMARY OF THE INVENTION

In accordance with the present invention, there is provided a process for the reductive dehalogenation of polyhaloaromatic compounds. This process comprises reacting polyhaloaromatics, in a hydrocarbon or silicone-based oil or an organic diluent, with an alkali metal in the presence of an ammonium salt. When this process is used, polyhaloaromatics contained in the oil or the organic diluent are reduced to environmentally safer hydrogenated aromatics while their halogen content is converted to metal halides. Preferably, a suspension containing 1° polyhaloaromatics and particularly polychlorobiphenyls (PCBs) in a hydrocarbon or silicone-based oil or an organic diluent and 2° the desired ammonium salt is reacted with an alkali metal to obtain the desired reduction. The reaction will preferably be carried out under an inert atmosphere (although dehalogenation does occur in the presence of air), at a temperature close to room temperature and at a pressure close to the atmospheric pressure. The inert atmosphere is mainly used to increase the safety of the reaction.

Alkaline earth metals, such as calcium, on the other hand, satisfactory dechlorinate PCBs without using ammonium salts but require the use of a polar solvent such as methanol.

Hence, when using the process of the present invention, biphenyl, initially formed from the reduction of PCBs, is rapidly reduced in the alkali/ammonium salt system of the present invention to give volatile hydrogenated biphenyls. These volatile products are easily separated by extraction or distillation for either incineration, biodegradation or recycling as commercial products. The formation of volatile chemicals makes the process of the present invention preferable over related technologies in which the final products obtained from PCBs dechlorination are either less volatile biphenyls and/or unidentified polymeric materials that are more difficult to incinerate.

The process of the present invention is therefore quite suitable to dehalogenate polyhaloaromatics. It may be used to dechlorinate PCBs and PCBz contained in electrical insulating oils and heat transfer fluids, to treat heavily PCB-contaminated liquid and solid waste by employing oil as a diluent and to treat various halogenated organic wastes including those of pesticides and wood preservatives.

Hence, the present invention provides a dehalogenation process which is simple and for which the coreagents to be used are cheap, commercially available and have no adverse effect on the environment. Further, the coreagents used in the present process and their by-products are water soluble which makes their separation from the reaction mixture by extraction with water cheap and practical. The process of the present invention is also expected to have a good potential for industrial applications such as lignin modification.

The process of the present invention will be more readily illustrated by referring to the following description.

DETAILED DESCRIPTION OF THE INVENTION

The present invention relates to a process for the reductive dehalogenation of polyhaloaromatic compounds such as PCBs and halogenated compounds used in pesticides and wood preservatives. This process involves dissolving the polyhaloaromatics in either a hydrocarbon or silicone-based oil or an organic diluent and to react that solution with an alkali metal in the presence of an ammonium salt. Preferably, a suspension containing the polyhaloaromatic solution and the ammonium salt will be reacted with the alkali metal and this will reduce the polyhaloaromatics to hydrogenated aromatics. Also, the halogen content of the polyhaloaromatics compounds will be converted to metal halides.

The amount of alkali metal used to efficiently perform the process of the present invention will usually vary from 5 to 10 fold excess based on the number of moles of halogen in the polyhaloaromatic compound to be reduced. The use of an excess alkali metal concentration will compensate for any losses should a side reaction between the metal and the ammonium salt take place to produce hydrogen. The amount of ammonium salt to be used is also ranging from 5 to 10 moles for each mole of the polyhaloaromatic compound to be reduced. The reaction will preferably be performed at temperatures near room temperature usually under atmospheric pressure and will be carried out under an inert atmosphere although the use of an inert atmosphere is not absolutely necessary. The time period required to completely dehalogenate the polyhaloaromatic compounds will depend on the alkali metal and the ammonium salt used but will usually vary between 4 and 24 hours.

The process of the present invention represents a novel development of what is known among chemists as the Birch Reduction. In a conventional or classical Birch reduction, gaseous ammonia is liquified in the presence of an alkali or alkaline earth metal to bring about a wide variety of organic reductions provided a proton source such as an alcohol is present in the reaction mixture. However, the use of ammonia gas warrants the use of special equipment and important safety precautions are normally required to carry out the reaction. For example, the reaction is either carried out at very low temperatures such as $-70°$ C. to handle ammonia, or above room temperature with the use of pressure reactors.

In the process of the present invention, some reaction parameters are changed to allow the desired dehalogenation to take place at ambient conditions without externally applying ammonia. A suspension of an alkali metal, preferably lithium or sodium, and an ammonium salt has been found to efficiently dechlorinate polyhaloaromatic compounds such as PCBs in hydrocarbon-based oils or organic diluents at room temperature and atmospheric pressure.

One of the essential features of the present invention resides in the simultaneous use of both an ammonium salt and an alkali metal. In the case of dehalogenation of polychloroaromatics such as PCBs, the starting materials of the process of the present invention lead to a reductive cleavage of the aryl-Cl bond and to partial saturation of the aromatic rings of PCBs to give the predominant reaction product cyclohexylbenzene. Hence, it seems that when a suspension containing an ammonium salt and a polyhaloaromatic solution is reacted with an alkali metal, it generates ammonia in situ and in a controlled manner. This is essential to carry out the required reduction under mild conditions. Whilst the mechanism of the present invention is not understood, the functions of both the ammonium salt and the alkali metal are believed to be as outlined below.

Ammonium salts

The use of ammonium salts apparently serves the process of the present invention in two ways. First, it seems that the ammonium salt, in the presence of both the electron-deficient polyhaloaromatic compound and the alkali metal, generates some ammonia which is an essential component to accelerate and complete the reduction cycle. Secondly, the ammonium salt, $NH_4X$, acts as a potential proton source to hydrogenate the dehalogenated polyhaloaromatics, thereby leading to the formation of relatively volatile products such as cyclohexylbenzene and cyclohexenylbenzene.

Hence, in contrast to a classical Birch Reduction, no alcohols or acids are required in the process of the present invention because the ammonium salts are to be used as potential hydrogen donors.

In the process of the present invention, a wide variety of ammonium salts may be used. Ammonium salts such as ammonium dihydrogen phosphate, ammonium bicarbonate, ammonium acetate, ammonium formate and the like may be employed, although it is to be understood that the present description is not intended to be limited to these products. The person skilled in the art will thus readily appreciate the importance of the dual function of the ammonium salt employed. The choice of a particular ammonium salt depends on considerations such as cost, ease of disposal of the products formed by the reduction process and time required to complete the reaction.

Alkali metals

The alkali metals that can be used in the context of the present invention are lithium, sodium or potassium with sodium and lithium being preferred. In most instances, the alkali metal will be added in the form of a fine dispersion that will be incorporated in the contaminated solution to be treated. It is to be understood that the size of the alkali metal particles to be used in the context of the present invention is not critical and not required to obtain substantial yields in the process.

Hence, the alkali metal may be added as a suspension in a suitable solvent, directly to the starting material in the form of a finely divided powder, or introduced into the reaction mixture in small pieces, free of any surface coatings. The process through which alkali metal dispersions are prepared is well known to those skilled in the art. Under similar conditions, alkaline earth metals such as calcium do not produce significant dehalogenation of polyhaloaromatics such as PCBs. Satisfactory dehalogenation is obtained after treating polyhaloaromatics such as PCBs with calcium granules in a polar solvent such as methanol. Preferably, at least two separate treatments of a PCB solution during which excess calcium, preferably a 20 fold excess based on the stoechiometric amount of the chlorine present in PCBs, will cause dehalogenation of the treated product.

Compounds to be dehalogenated according to the process of the present invention The products that may be dehalogenated using the process of the present invention are halogenated aromatic compounds or mixtures containing such compounds. These compounds include halogenated benzenes, halogenated biphenyls and halogenated polynuclear aromatics.

In most instances, the compounds will be polychlorinated biphenyls, either alone or as mixtures with hydrocarbon or silicone-based oils such as transformer oils, ballast oils, heat transfer fluids, or lubricants. The compounds to be treated may also include contaminated solid wastes previously treated with a suitable diluent and various halogenated organic wastes including those of pesticides and wood preservatives.

The dehalogenation process

The process of the present invention is generally carried out in the following manner. A suspension containing between 5 and 10 moles of an ammonium salt for each mole of the polyhaloaromatic compound to be reduced is prepared either in a hydrocarbon based oil such as paraffin oil or a suitable organic diluent such as THF.

To this suspension, a dispersion of alkali metal such as lithium or sodium is added at a temperature close to room temperature or in an ice cooled bath, which may be under an inert atmosphere. A nitrogen atmosphere has been found to be suitable. Normally, the amount of alkali metal will be added in excess of the stoechiometric amount of the polyhalogenated aromatics based on the molar halogen content of the polyhaloaromatic.

Once the alkali metal dispersion has been added, the mixture may be stirred at room temperature for a time that will range from 4 to 24 hours. Although not necessary, it has been found that sonication at 50 to 60 Hz and/or gentle warming at a temperature below the boiling point of the solvent, that is usually between 40° to 60° C. enhance the rate of dehalogenation and reduce the time required to complete the reduction process.

Once the dehalogenation reaction is substantially completed, a termination agent may be added to remove from the system any excess alkali metal remaining after the reaction with the polyhaloaromatic compound. The termination agent is a hydrated absorbent material that, when added to the system, will react with any unreacted alkali metal. Among the suitable termination agents that may be used, one may mention water, alkanols, glycols, phenols, especially polyhydric phenols, carbon dioxide (gas or solid) and mixtures thereof. Usually, these agents will form a separate phase from the dehalogenated material and can be separated. Some of these agents, particularly aqueous media, also serve as extractants to remove the alkali metal halide reaction product. The aqueous media forms a separate phase which is readily removed and is suitable for disposal.

Thus, once the protic termination solvent has been added to the solution through careful and moderate additions with occasional cooling in an ice cooled bath, the reaction mixture is subsequently partitioned into two phases, a water phase that contains the halide ions and the ammonium salts, and an organic phase that contains the non-halogenated and hydrogenated biphenyls.

The organic phase may then be analyzed through GC and GC/MS analysis. In the case of PCBs for example, the disappearance of polychlorinated biphenyl may be followed using a Perkin-Elmer, Sigma 2000 gas chromatograph mounted with an electron capture detector, ECD and a DB5-fused silica capillary column (30 m×0.248 mm). The products from the dechlorination process may be identified on a GC/MSD (HP 5970 MSD series), and when available by comparison with authentic samples. Quantification of products may be carried out on a Perkin-Elmer, Sigma 2000 gas chromatograph mounted with a flame ionization detector, FID. For example, an Ultra-1 fused silica capillary column (50 m×0.2 mm) may be used for the analysis as was the case for the present invention. As for the aqueous phase, it can be analyzed for halide ion content using HPLC-ion chromatography.

The process of the present invention, whether carried out as a continuous or batch process, is simple and general and it has an excellent potential for industrial applications such as lignin modification.

In the present invention, aromatic compounds such as biphenyls are not usually eventual products. In fact, extensive hydrogenation of the dechlorinated biphenyl moiety of PCBs for example takes place to give cyclohexylbenzene as a main product as well as minor amounts of cyclohexenylbenzene and other dihydrobiphenyls. These organic products are volatile and can be easily separated from the reaction mixture by simple extraction, distillation or evaporation under reduced pressure. The isolated organics may be recycled as commercial products or safely incinerated.

The remaining products are mainly non-toxic ammonium and halide salts that are easily extracted with water. Hence, the process of the present invention permits the establishment of a mass balance in which halogen content and organic products from polyhaloaromatics can be identified and analyzed using readily available analytical equipment.

The present invention will be further illustrated by referring to the following examples which are given by way of illustration and not by way of limitation. As shown in these examples, substantially all of the polyhaloaromatics contents of the solutions treated using the process of the present invention are reduced to halogenated aromatics while substantially all their halogen content is converted to metal halides.

Example 1

Dechlorination of 4-Cl-biphenyl 0.35 g of 4-Cl-biphenyl, 0.14 g of lithium powder and 25 ml of tetrahydrofuran were charged in a three necked round bottom flask equipped with a water cooled condenser, a teflon-coated septum, a gas inlet and a magnetic stirring bar. The mixture was stirred in an ice cooled bath to allow the addition of 1.9 g of solid ammonium acetate. The resulting mixture was stirred under nitrogen at ambient temperature for 12 hours. The colourless reaction mixture was cooled in an ice bath while 10 ml of methanol were gently added from a dropping funnel. The mixture was then stirred for 1 hour to give a homogenous colourless solution. Solvents were evaporated on a rotary pump. The remaining white solid was partitioned between 50 ml of doubly deionized water and 50 ml of pesticide grade hexane. The water and hexane fractions were back-washed with 50 ml of hexane and 50 ml of water respectively. Hexane fractions were combined together, spiked with hexadecane as internal standard and dried over anhydrous magnesium sulfate for GC and GC/MS analysis.

The water phase was analyzed for chloride ion content using HPLC-Ion chromatography. A SP8100 HPLC coupled with Waters model 430 conductivity detector is used. The recovery of the chloride ion was 100%. The GC and GC/MS analysis indicated the complete disappearance of 4-Cl-biphenyl and the formation of cyclohexylbenzene in a proportion exceeding 90%. Biphenyl was formed in a proportion below 2% and the longer biphenyl stays in contact with the ammonium salt and lithium the more it is hydrogenated to give the cyclohexyl derivatives. Some high molecular weight products (approximately 5%) are observed whose parent ion are similar to the molecular weights of hydrogenated biphenyl dimers, that is m/e 318.

Examples 2 to 6

In the following examples, the PCBs that have been used were obtained from Chem. Service, USA and are sold under the trade name Arochlor 1242, Arochlor 1248 and Arochlor 1254.

Example 2

Dechlorination of Arochlor 1248 using ammonium acetate.

0.25 g of Arochlor 1248 was dechlorinated in the presence of 0.3 g of lithium and 3.4 g of ammonium acetate in 25 ml of tetrahydrofuran following the procedure outlined in Example 1.

Chloride analysis by HPLC-ion chromatography indicated that 100% of the total content of chlorine which was evaluated at 48% by weight in Arochlor 1248, is obtained as chloride ions in the aqueous phase. GC and GC/MS analysis indicated that all Arochlor 1248 disappeared and the non-chlorinated products cyclohexylbenzene and cyclohexenylbenzene formed as major products, accompanied by 5% of biphenyl. Traces of hydrogenated biphenyl dimers and products from the solvent are also detected. In all, the total recovery of the organic material was larger than 95%.

Example 3

Dechlorination of Arochlor 1248 using ammonium formate.

0.19 g of Arochlor 1248 was dechlorinated in the presence of 0.18 g of lithium and 1.8 g of ammonium formate in 25 ml of tetrahydrofuran following the procedure outlined in Example 1. At the end of the 12 hour dechlorination period, the reaction products were worked up as described in Example 1.

Ion chromatography showed that close to 100% of the chlorine content of Arochlor 1248, given the fact that 48% of the total weight of Arochlor 1248 is chlorine, is present in the water phase. GC-ECD and GC/MS showed complete disappearance of the PCBs and the formation of hydrogenated biphenyl products.

Example 4

Dechlorination of Arochlor 1248 using ammonium bicarbonate.

0.19 9 of Arochlor 1248 was dechlorinated in the presence of 0.4 g of lithium and 1.8 g of ammonium bicarbonate in 25 ml of tetrahydrofuran following the procedure outlined in Example 1, except for the fact that the solution was sonicated at 50 Hz and heated at 40° C.

Chloride ion analysis showed quantitative recovery of all the chlorine content in the Arochlor 1248 and the GC and GC/MS analysis showed the complete disappearance of Arochlor 1248.

Example 5

Dechlorination of Arochlor 1242.

0.13 g of Arochlor 1242, 1.4 g of ammonium acetate and 0.13 g of lithium in 20 ml of tetrahydrofuran were treated in the matter outlined in Example 1. At the end of the 12 hour dechlorination reaction, the reaction products were analyzed.

Chloride ion analysis by ion chromatography showed that close to 100% of the chlorine content of Arochlor 1242, which contains 42% of chlorine, is present in the aqueous phase. GC and GC/MS analysis failed to reveal Arochlor 1242 and indicated the formation of cyclohexylbenzene as a major product. Traces of biphenyl, 1 4-dihydrobiphenyl and products from the solvent were also detected. In all, the hydrogenated biphenyl products account for more than 95% of the total organic content of Arochlor 1242.

Example 6

Dechlorination of Arochlor 1254.

0.15 g of Arochlor 1254, 0.14 g of lithium and 2.5 g of ammonium acetate in 25 ml of tetrahydrofuran were treated in the manner outlined in Example 1.

GC and GC/MS analysis showed complete disappearance of Arochlor 1254 and a recovery of all the chlorine content in the PCB as chloride anions in the aqueous phase.

Example 7

Dechlorination of Arochlor 1248 using calcium in methanol.

To 0.23 g of Arochlor 1248 in 100 ml of methanol, 2.0 g of calcium were added under a nitrogen atmosphere at room temperature. The mixture was then stirred and immediate reaction took place. After the disappearance of calcium, that is approximately 40 minutes, a 200 ul sample was taken out, neutralized with 0.5 ml of water and then extracted with 1 ml of hexane. GC analysis indicated disappearance of about 50% of the PCBs. The reaction mixture was then subjected to a second treatment outlined as follows.

Unreacted PCBs and their organic products were extracted into hexane and hexane was subsequently evaporated on a water pump. The residual untreated PCBs were dissolved in 100 ml of methanol and treated with 2.0 g of calcium for 1 hour at room temperature. The reaction mixture was worked up as described above. GC analysis showed disappearance of more than 95% of the PCBs whereas biphenyl, mono-chlorobiphenyl and di-chlorobiphenyl formed in almost equal amounts.

Claims to the invention follow.

1. A process for the reductive dehalogenation of polyhaloaromatic compounds which comprises reacting polyhaloaromatics, in a hydrocarbon or silicone-based oil or an organic diluent, with an excess alkali metal in the presence of an ammonium salt to reduce the polyhaloaromatics to hydrogenated aromatics and to convert the halogen content to metal halides.

2. A process according to claim 1, wherein said polyhaloaromatics and said ammonium salt are reacted with said alkali metal in the form of a suspension.

3. A process according to claim 1, wherein the amount of alkali metal ranges from 5 to 10 fold excess based on the number of moles of halogen in the polyhaloaromatic compound to be reduced and the amount of ammonium salt ranges from 5 to 10 moles for each mole of the polyhaloaromatic compound to be reduced.

4. A process according to claim 1, wherein the reaction is carried out under an inert atmosphere.

5. A process according to claim 4, wherein the inert atmosphere is a nitrogen atmosphere.

6. A process according to claim 1, wherein the reaction is carried out at a temperature ranging from 40° to 60° C.

7. A process according to claim 1, wherein the polyhaloaromatic compound is a polychlorinated biphenyl.

8. A process according to claim 1, wherein the ammonium salt is selected from the group consisting of ammonium dihydrogen phosphate, ammonium acetate, ammonium formate and ammonium bicarbonate.

9. A process according to claim 1, wherein the alkali metal is selected from the group consisting of sodium and lithium.

10. A process according to claim 9, wherein the alkali metal is added in the form of a fine dispersion, or in small pieces free of surface coatings.

* * * * *